United States Patent [19]

Schmid

[11] Patent Number: 5,142,069

[45] Date of Patent: Aug. 25, 1992

[54] PROCESS OF PREPARING 2,2-DIMETHYL-2,3-DIHYDROBENZOFURAN-7-CARBOXYLIC ACIDS

[75] Inventor: Christopher R. Schmid, Indianapolis, Ind.

[73] Assignee: Eli Lilly and Company, Indianapolis, Ind.

[21] Appl. No.: 666,279

[22] Filed: Mar. 7, 1991

[51] Int. Cl.$^5$ .............................................. C07D 307/87
[52] U.S. Cl. .................................... 549/462; 549/466
[58] Field of Search ............................... 549/462, 466

[56] References Cited

U.S. PATENT DOCUMENTS 3,860,619  1/1975  Christensen et al. ............... 549/462
4,921,982  5/1990  Cohen et al. ........................ 549/462

FOREIGN PATENT DOCUMENTS 147044  7/1985  European Pat. Off. .
234872  9/1987  European Pat. Off. .
84/03281  8/1984  PCT Int'l Appl. .

OTHER PUBLICATIONS

Brewster, et al. *Organic Chemistry*, Third Edition p. 247, Prentice-Hall, Inc. (1962).
Morrison, et al. *Organic Chemistry*, Third Edition pp. 677–681, Allyn and Bacon, Inc. (1975).
Occelli, et al., *Gazz. Chim. Ital.*, 8(9–10), 383 (1981).
Loev, *Chemistry and Industry*, 193 (Feb. 1, 1964).

Primary Examiner—C. Warren Ivy
Assistant Examiner—P. G. Spivack
Attorney, Agent, or Firm—Joseph A. Jones; Leroy Whitaker; Robert A. Conrad

[57] ABSTRACT

This invention provides a process and intermediates for preparing 2,2-dimethyl-2,3-dihydrobenzofuran-7-carboxylic acids.

6 Claims, No Drawings

PROCESS OF PREPARING 2,2-DIMETHYL-2,3-DIHYDROBENZOFURAN-7-CARBOXYLIC ACIDS

BACKGROUND OF THE INVENTION

U.S. Pat. No. 4,921,982 describes a series of bicyclic carboxylic esters and amides which are reported to be specific $5HT_3$ antagonists. Many of the preferred compounds in this reference have a bicyclic nucleus of the 2,2-dimethyl-2,3-benzofuran-7-carboxylic acid type. See, e.g., Formula Ia and appropriate intermediates of Formula IIa.

The process for preparing the carboxylic acid intermediates required for the synthesis of the esters and amides provided by this patent is disclosed in Scheme 2 of this reference. In the case of the oxygen-containing bicyclic system a minimum of 5 steps is required to convert the phenol-ester of Formula IV to the corresponding bicyclic carboxylic acid of Formula II. The protection and deprotection of the acid functionality are two steps required by this scheme which can adversely affect yield and otherwise add to the overall economy of preparing such intermediates.

Similar chemistry is also reported for related compounds; see, e.g., Reaction Schemes I and II in each of EPO Patent Application Publications 147044 and 234872.

It has now been discovered that many of the preferred intermediates reported in U.S. Pat. No. 4,921,982 can be prepared in a 3-step sequence from ortho-hydroxy benzoic acids in high yield.

SUMMARY OF THE INVENTION

This invention provides a process for preparing 2,2-dimethyl-2,3-dihydrobenzofuran-7-carboxylic acids of Formula I

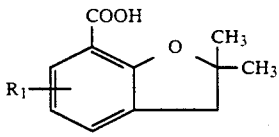

wherein
$R_1$ is hydrogen, methyl, halo, $C_1$-$C_3$ alkoxy, ($C_1$-$C_3$ alkyl)—S(O)$_t$—, trifluoromethyl, or $(CH_3)_2NSO_2$—, and t is 0, 1, or 2; which comprises the concomitant cyclization and acid-catalyzed

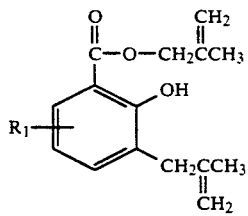

in the presence of an organic acid.

Also provided by this invention are the methallyl esters of Formula II which are intermediates in the preparation of compounds of Formula I.

Also provided by this invention are the methallyl esters of Formula III

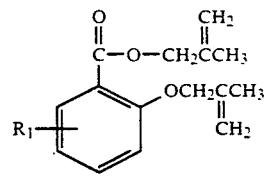

which are useful as precursors to the compounds of Formula II.

DETAILED DESCRIPTION AND PREFERRED EMBODIMENTS

The functionalities and substituents defined as $R_1$ above are generally the same as provided in U.S. Pat. No. 4,921,982, with certain exceptions, which reference is expressly incorporated into this application.

According to the process provided by this invention, the intermediates of Formula II are converted into the compounds of Formula I. This process accomplishes two concomitant steps—the cyclization of the methallyl group with the phenol to provide the dimethyl-substituted 5-membered ring which forms part of the dihydrobenzofuran nucleus of Formula I, and deprotection of the methallyl ester of Formula II to the corresponding carboxylic acid. This latter step appears to be without any precedent in literature.

The process of transforming compound II into the desired intermediate I is usually accomplished in approximately 70-80% yield when compound II is heated at reflux for 8 to about 17.5 hours in the presence of an organic acid. Such organic acids can include alkanoic acids such as formic acid, acetic acid, butyric acid, valeric acid, and the like, hydroxy-substituted alkanoic acids, such as 3-hydroxybutyric acid and 12-hydroxydodecanoic acid, alkanedioic acids, such as oxalic acid and maleic acid, alkenoic acids, such as acrylic acid, aromatic acids such as benzoic acid, 2-, 3-, or 4-hydroxybenzoic acid, o-, m-, or p-toluic acid, haloacetic acids, such as trifluoroacetic acid, and the like. Preferred organic acids are those which are liquid at ambient temperature and whose boiling point at least about 100° C. Preferred acids are acetic and especially formic acid. The addition of small amounts of water is advantageous to prevent the formation of and/or to decompose acid anhydrides in the reaction mixture. Up to a molar equivalent of water (based upon the amount of organic acid employed) may be added to the reaction mixture. Thus, although anhydrous formic acid may be employed, it is preferred that either 98% or especially 90% formic acid be used in the process of this invention. When the reaction is performed at approximately 100° C., the reaction is generally complete after approximately 8-12 hours.

The phenol intermediates of Formula II are prepared from the compounds of Formula III. This transformation, as generally reported in the aforementioned reference, is generally known as a Claisen rearrangement and is accomplished by heating compound III to temperatures of about 150-200° C., preferably in the presence of a non-reactive solvent. Such solvents include 1-methyl-2-pyrrolidinone, xylenes, ethylbenzene, dimethylformamide, and the like. When 1-methyl-2-pyrrolidinone is employed as the solvent, the transformation is generally complete in approximately 6 hours when heated at reflux temperature.

The intermediates of Formula III are prepared from the corresponding $R_1$-substituted salicylic acids upon alkylation with methallyl halides. This is accomplished by allowing the R₁-substituted salicylic acid to react in the presence of at least two molar equivalents of a methallyl halide, such as methallyl chloride, in the presence of a non-reactive solvent, in particular a dipolar aprotic solvent such as dimethylformamide (DMF), dimethylsulfoxide (DMSO), or 1-methyl-2-pyrrolidinone. This transformation is best carried out in the presence of a base, such as an inorganic base, e.g., potassium carbonate or sodium hydroxide. It is preferred that the transformation be carried out at temperatures from approximately ambient temperature up the reflux temperature of the reaction mixture; temperatures from approximately 60–90° C. are most preferred; under these conditions, the alkylation is usually complete in 24–72 hours.

All of the compounds of Formula I, except for that wherein $R_1$ is hydrogen, are intermediates to compounds as found in U.S. Pat. No. 4,921,982. The compound of Formula I wherein $R_1$ is hydrogen can be used as an intermediate to other intermediates of Formula I or final compounds of the referenced patent. For example, the compound of Formula I wherein $R_1$ is hydrogen can be transformed into the corresponding compound wherein $R_1$ is chloro by aromatic chlorination, a process well known to skilled artisans.

The following examples further illustrate the preparation of the intermediates and process of this invention. The examples are illustrative only and are not intended to limit the scope of the invention in any way.

EXAMPLE 1

5-chloro-2-[(2-methyl-2-propenyl)oxy]benzoic acid 2-methyl-2-propenyl ester

Twenty milliliters of dimethylformamide were heated to 60° C. To the solvent were added 2.1 g of 5-chloro-2-hydroxybenzoic acid and 3.8 g of potassium carbonate. After the additions were complete, 2.65 ml of methallyl chloride were added to the reaction mixture and the solution maintained at 60° C. overnight. The reaction mixture was cooled and partitioned between water and ethyl acetate. The organic layer was separated, washed sequentially with a sodium bicarbonate solution, and sodium chloride solution, dried over magnesium sulfate, filtered, and concentrated in vacuo to provide 3.0 g of the desired title intermediate as a yellow oil. Proton nuclear magnetic resonance indicated some residual dimethylformamide.

When this reaction was repeated employing 2.77 Kg of 5-chloro-2-hydroxybenzoic acid, 7.6 liters of dimethylformamide, 5.55 Kg of potassium carbonate, and 3.96 liters of methallyl chloride, the cooled reaction mixture was filtered and divided into two portions. Each portion was poured separately into a mixture of 2.8 liters of hexane, 1.4 liters of ethyl acetate and 7 liters of water. The layers were separated and the aqueous layer in each case extracted again with a mixture of 1.4 liters of hexane and 0.7 liters of ethyl acetate. The organic fractions were combined and washed with 4.1 liters of water followed by a sodium chloride solution of 800 grams of sodium chloride in 4.1 liters of water. The organic extracts were combined, dried over magnesium sulfate, filtered and concentrated in vacuo to provide 4.21 Kg of the desired intermediate.

¹H NMR (300 MHz, CDCl₃): δ 7.79 (d, 1H), 7.36 (dd, 1H), 6.88 (d, 1H), 5.10 (d, 2H), 4.98 (d, 2H), 4.72 (s, 2H), 4.48 (s, 2H), 1.8 (s, 6H).

EXAMPLE 2

5-chloro-2-hydroxy-3-(2-methyl-2-propenyl)benzoic acid 2-methyl-2-propenyl ester A mixture of 0.9 g of 5-chloro-2-[(2-methyl-2-propenyl)oxy]benzoic acid 2-methyl-2-propenyl ester and 1 ml of N-methylpyrrolidone were heated to 200° C. under a nitrogen atmosphere. After 1.5 hours the reaction mixture was cooled and partitioned between a 4:1 hexane/ethyl acetate and water mixture. The layers were separated and the organic layer washed with water and a saturated sodium chloride solution, dried over magnesium sulfate, filtered and concentrated in vacuo to provide 0.8 g of the desired title intermediate as a brown oil.

The reaction was repeated by heating 6.102 Kg of the methallyloxy intermediate in 6.1 liters of N-methylpyrrolidone for approximately 7 hours. The mixture was cooled and divided into 2 equal portions. Each portion was treated with 2 liters of hexane, 1 liter of ethyl acetate and 6 liters of water. In each case the layers were allowed to separate. The aqueous layer in each case was further extracted with 1 liter of hexane and 0.5 liters of ethyl acetate. The combined organic extracts from each portion were washed with 3 liters of water. The washed organic layers from each portion was combined, dried over magnesium sulfate, and concentrated to dryness to provide 5,697 g of the title intermediate.

¹H NMR (300 MHz, CDCl₃): δ 7.74 (d, 1H), 7.29 (d, 1H), 5.05 (d, 2H), 4.78 (d, 2H), 4.77 (s, 2H), 3.38 (s, 2H), 1.82 (s, 3H), 1.73 (s, 3H).

EXAMPLE 3

5-chloro-2,2-dimethyl-2,3-dihydro-7-benzofurancarboxylic acid

A mixture of 7.02 g of 5-chloro-2-hydroxy-3(2-methyl-2-propenyl)benzoic acid 2-methyl-2-propenyl ester and 21 ml of 90% formic acid was heated at reflux overnight. After cooling, the reaction mixture was partitioned between 100 ml of ethyl acetate and 100 ml of water. The layers were separated and the organic layer washed twice more with 80 ml portions of water. The organic layer was extracted 3 times with a saturated sodium bicarbonate solution. The aqueous layers were combined, acidified with 12N hydrochloric acid, and the resulting precipitate recovered by filtration. The precipitate was washed with water and dried at 60° C. to provide 4.11 g of the desired title intermediate.

When this experiment was repeated on a larger scale, 3.8 Kg of the phenol were heated at approximately 103–105° C. in 11.4 liters of 90% formic acid. After maintaining this temperature for 17.5 hours, approximately 7.4 liters of formic acid were allowed to distill off. The remaining solution was cooled to 78° C. and 6.5 liters of toluene were added. The remaining formic acid was distilled off as a toluene/formic acid azeotrope; 12.4 liters of formic acid and 700 ml of toluene were recovered. The remaining solution was cooled to approximately 0° C. and the resulting crystalline solid recovered by filtration. The solid was washed with toluene and dried 35–40° C. for approximately 20 hours providing 2,334 g of the desired title intermediate, m.p. 159–161° C.

Analysis for: $C_{11}H_{11}ClO_3$:
Calculated: C: 58.29; H: 4.89;
Found: C: 58.19; H: 4.93.

$^1$H NMR (300 MHz, CDCl$_3$): δ 10.65 (br s, 1H), 7.79 (s, 1H), 7.30 (s, 1H), 3.04 (s, 2H), 1.59 (s, 6H).

$^{13}$C NMR (300 MHz, CDCl$_3$): δ 166.6, 157.6, 131.2, 130.5, 129.7, 125.5, 113.0, 91.3, 42.0, 28.1.

I claim:

1. A process for preparing a compound of Formula I

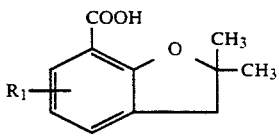

wherein R$_1$ is hydrogen, methyl, halo, C$_1$–C$_3$ alkoxy, (C$_1$–C$_3$ alkyl) —S(O)$_t$—, trifluoromethyl, or (CH$_3$)$_2$NSO$_2$—, and t is 0, 1, or 2, which comprises heating a phenol of Formula II

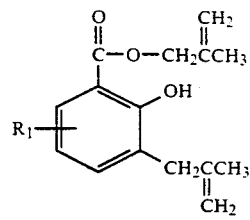

in the presence of an organic acid.

2. The process of claim 1 wherein the organic acid is formic acid.

3. The process of claim 1 wherein R$_1$ is chloro.

4. The process of claim 3 wherein the compound of Formula II is 5-chloro-2-hydroxy-3-(2-methyl-2-propenyl)benzoic acid 2-methyl-2-propenyl ester.

5. The process of claim 4 wherein the organic acid is formic acid.

6. The process of claim 5 wherein the organic acid is 90% formic acid.

* * * * *